United States Patent
Trayanova et al.

(10) Patent No.: US 9,662,027 B2
(45) Date of Patent: May 30, 2017

(54) METHODOLOGY FOR ASSESSING THE BOUNDED-INPUT BOUNDED-OUTPUT INSTABILITY IN QT INTERVAL DYNAMICS: APPLICATION TO CLINICAL ECG WITH VENTRICULAR TACHYCARDIA

(71) Applicant: THE JOHNS HOPKINS UNIVERSITY, Baltimore, MD (US)

(72) Inventors: Natalia Trayanova, Baltimore, MD (US); Xiaozhong Chen, Hoover, AL (US)

(73) Assignee: The Johns Hopkins University, Baltimore, MD (US)

( * ) Notice: Subject to any disclaimer, the term of this patent is extended or adjusted under 35 U.S.C. 154(b) by 234 days.

(21) Appl. No.: 14/405,812

(22) PCT Filed: Jun. 5, 2013

(86) PCT No.: PCT/US2013/044216
§ 371 (c)(1),
(2) Date: Dec. 5, 2014

(87) PCT Pub. No.: WO2013/184745
PCT Pub. Date: Dec. 12, 2013

(65) Prior Publication Data
US 2015/0141861 A1    May 21, 2015

Related U.S. Application Data

(60) Provisional application No. 61/655,803, filed on Jun. 5, 2012.

(51) Int. Cl.
*A61B 5/04* (2006.01)
*A61B 5/0402* (2006.01)
(Continued)

(52) U.S. Cl.
CPC ........ *A61B 5/04012* (2013.01); *A61B 5/0245* (2013.01); *A61B 5/0402* (2013.01);
(Continued)

(58) Field of Classification Search
CPC ... A61B 5/0452; A61B 5/7275; A61B 5/0004; A61B 5/0006
See application file for complete search history.

(56) References Cited

U.S. PATENT DOCUMENTS

| | | | |
|---|---|---|---|
| 2004/0006265 A1* | 1/2004 | Alhusseiny | A61B 5/0402 600/386 |
| 2007/0244402 A1 | 10/2007 | Brockway et al. | |

(Continued)

FOREIGN PATENT DOCUMENTS

WO    2011-084636 A2    7/2011

*Primary Examiner* — Edward Moran
*Assistant Examiner* — Natasha Patel
(74) *Attorney, Agent, or Firm* — Johns Hopkins Technology Ventures

(57) ABSTRACT

The present invention is directed to a method for determining onset of ventricular arrhythmias using bounded-input bounded-output stability of QT interval (QTI) dynamics. The method of the present invention includes two parts. A first part of the method determines the dependence of each QTI on several prior QTIs and RR intervals (RRI). This determination is represented as an autoregressive model with exogenous input (ARX). A second part of the method determines the BIBO stability of the ARX model in the z-domain. The metrics associated with the first and second parts of the method are then used to predict onset of arrhythmia.

21 Claims, 6 Drawing Sheets

(51) Int. Cl.
  *A61B 5/0452* (2006.01)
  *A61B 5/0464* (2006.01)
  *A61B 5/0245* (2006.01)
  *A61B 5/0432* (2006.01)
  *A61B 5/0456* (2006.01)
  *A61B 5/0468* (2006.01)

(52) U.S. Cl.
  CPC .......... *A61B 5/0432* (2013.01); *A61B 5/0452* (2013.01); *A61B 5/0456* (2013.01); *A61B 5/0464* (2013.01); *A61B 5/0468* (2013.01)

(56) References Cited

U.S. PATENT DOCUMENTS

| | | |
|---|---|---|
| 2008/0114411 A1 | 5/2008 | Lian et al. |
| 2009/0228061 A1 | 9/2009 | Lian et al. |
| 2009/0299424 A1* | 12/2009 | Narayan .............. A61B 5/0402 607/9 |
| 2011/0190650 A1 | 8/2011 | McNair |

* cited by examiner

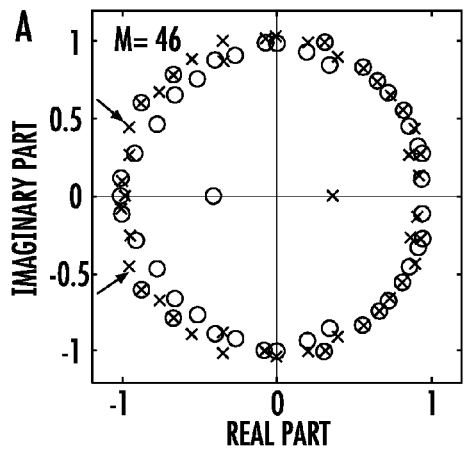
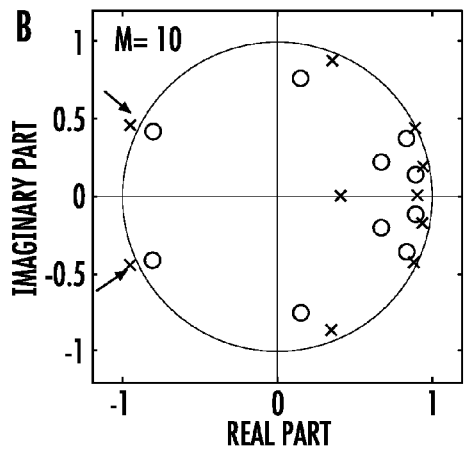
FIG. 4A  FIG. 4B
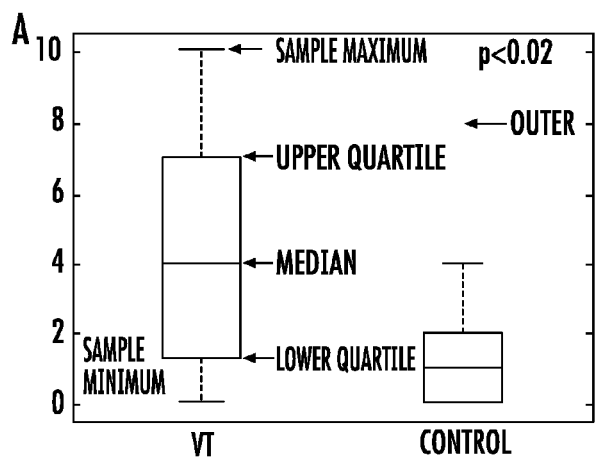
FIG. 5A
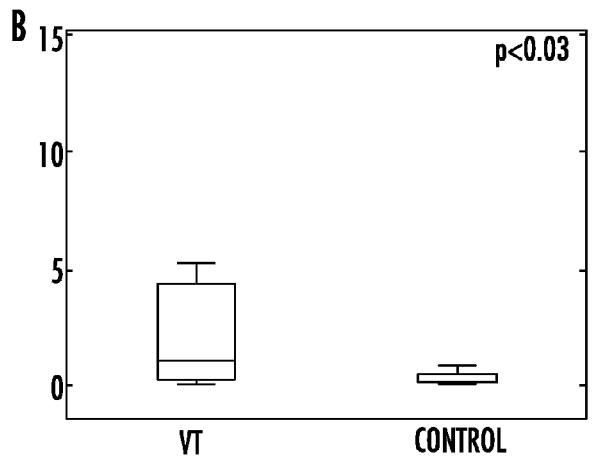
FIG. 5B

METHODOLOGY FOR ASSESSING THE BOUNDED-INPUT BOUNDED-OUTPUT INSTABILITY IN QT INTERVAL DYNAMICS: APPLICATION TO CLINICAL ECG WITH VENTRICULAR TACHYCARDIA

CROSS-REFERENCE TO RELATED APPLICATIONS

This application is a 35 U.S.C. §371 U.S. national entry of International Application PCT/US2013/044216, having an international filing date of Jun. 5, 2013, which claims the benefit of U.S. Provisional Application No. 61/655,803, filed Jun. 5, 2012, the content of each of the aforementioned applications is herein incorporated by reference in their entirety.

GOVERNMENT SUPPORT

This invention was made with government support under HL082729 awarded by the National Institutes of Health. The government has certain rights in the invention.

FIELD OF THE INVENTION

The present invention relates generally to cardiac health. More particularly, the present invention relates to a system and method for determining QT interval dynamics.

BACKGROUND OF THE INVENTION

Sudden cardiac death (SCD) is a major health problem in the industrialized world. SCD often occurs in healthy individuals without prior history of heart disease. The early diagnosis of arrhythmia has the potential to significantly reduce mortality due to SCD. Unstable dynamics of cardiac repolarization plays an important role in the mechanisms of arrhythmia. It has been widely reported that unstable dynamics of action potential duration (APD), the latter a measure of cardiac repolarization at the cellular level, is responsible for wave break-up and the initiation of arrhythmia. At the organ level, the QT interval (QTI) in the ECG is a global manifestation of the ventricular repolarization. Unstable QTI dynamics in an ECG recording has been linked to arrhythmia susceptibility in patients with different cardiac diseases, such as long QT syndrome, acute myocardial infarction, and dilated cardiomyopathy.

APD has been studied as a function of its preceding diastolic interval (DI), a relationship known as APD restitution. The slope of APD restitution has been used as an indicator of the instability in APD dynamics. It is known that given a large (>1) APD restitution slope, a small perturbation in DI (a bounded input) causes diverging oscillations in APD (an unbounded output). In other words, the slope of the APD restitution curve is considered to determine the Bounded-Input Bounded-Output (BIBO) stability of APD dynamics. If a system is BIBO-stable, then the output will be bounded for every bounded input to the system; otherwise, the system is considered BIBO-unstable.

The contribution of APD restitution to arrhythmogenesis has been extensively studied over the past decade. It has been widely reported that unstable APD dynamics causes the failure of activation, increases the gradient in APD distribution, initiates ventricular tachycardia (VT), and causes the transition from VT to ventricular fibrillation (VF). However, studies have reported that APD restitution slope is not always a predictor of arrhythmia occurrence. This failure has been attributed to the presence of short term memory, i.e. the dependence of APD on activation history prior to the preceding DI. In restitution studies, a constant pacing train is usually applied so that the response to the initial conditions (the activation history prior to constant pacing) dies out during the pacing, thus eliminating the contribution of short-term memory to APD dynamics. However, research has demonstrated that the presence of short-term memory can either enhance or suppress APD instability. In the case when the contribution of short term memory cannot be eliminated by the pacing protocol, APD restitution slope is not a reliable measure of BIBO stability in APD dynamics, and thus cannot be used to predict the onset of arrhythmia.

Based on the concept of APD restitution, QTI restitution, which is the dependence of QTI on the preceding TQ interval (TQI), has been studied using clinical ECG recordings. Increased QTI restitution slope revealing BIBO-unstable QTI dynamics has been reported in diseased human hearts. Similar to APD restitution, QTI restitution is usually assessed under invasive constant pacing protocols that eliminate short-term memory. However, the heart rhythm preceding arrhythmia onset is typically non-constant, and thus the contribution of short-term memory to QTI dynamics and arrhythmia initiation cannot be ignored. Currently, there is no reliable way to detect BIBO instability in QTI dynamics from the clinical ECG recording without pacing to eliminate short term memory.

Accordingly, there is a need in the art for a method for assessing the level of BIBO stability in QTI dynamics without the need to eliminate the contribution of short-term memory.

SUMMARY OF THE INVENTION

The foregoing needs are met, to a great extent by a method of predicting ventricular arrhythmias, including receiving an electrical signal from a subject's heart for a predetermined period of heart beats. The method includes modeling QT interval (QTI) dynamics for the electrical signal for the predetermined period of heart beats. The method also includes assessing a level of bounded-input bounded-output (BIBO) stability for the QTI dynamics. Additionally, the method includes predicting ventricular arrhythmias for the subject based on the QTI dynamics and BIBO stability for the predetermined period.

In accordance with an aspect of the present invention, a medical device includes a system for predicting ventricular arrhythmias, said system including a data processor configured to receive an electrical signal from a subject's heart for a predetermined period of heart beat. The data processor is also configured to model QT interval (QTI) dynamics for the electrical signal for the predetermined period of heart beats. Additionally, the data processor is configured to assess a level of bounded-input bounded-output (BIBO) stability for the QTI dynamics and predict ventricular arrhythmias for the subject based on the QTI dynamics and BIBO stability for the predetermined period.

In accordance with another aspect of the present invention, a fixed computer readable medium includes stored executable instructions for execution by a computer, including executable instructions for receiving an electrical signal from a subject's heart for a predetermined period of heart beats. The stored executable instructions also include modeling QT interval (QTI) dynamics for the electrical signal for the predetermined period of heart beats. Additionally, the stored executable instructions include assessing a level of bounded-input bounded-output (BIBO) stability for the QTI dynamics and predicting ventricular arrhythmias for the subject based on the QTI dynamics and BIBO stability for the predetermined period.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 4A and 4B illustrate a graphical view of a pole zero plot of a minECG for different values of M. FIG. 4A illustrates $M_{max}$=46 and FIG. 4B illustrates $M_{min}$=10.

FIGS. 5A and 5B illustrate graphical views of comparisons of a median of $N_{us}$ and $f_{PA}$ respectively.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method for determining onset of ventricular arrhythmias using bounded-input bounded-output stability of QT interval (QTI) dynamics. The method of the present invention includes two parts. A first part of the method determines the dependence of each QTI on several prior QTIs and RR intervals (RRI). This determination is represented as an autoregressive model with exogenous input (ARX). A second part of the method determines the BIBO stability of the ARX model in the z-domain. The metrics associated with the first and second parts of the method are then used to predict onset of arrhythmia.

Figure 1:
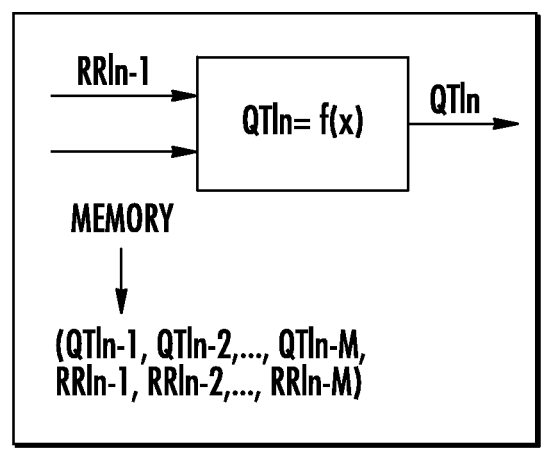
FIG. 1 is a schematic illustration of a system and method according to an embodiment of the current invention. In an embodiment, the QT interval (QTI) is a function of the preceding TQ interval (TQI), or equivalently of the preceding RR interval (RRI) since RRI=QTI+TQI, and memory. Memory is represented by the QTIs and RRIs (or TQIs) of M previous beats.

FIG. 1 schematically represents a medical device according to some embodiments of the current invention, which includes a system for predicting ventricular arrhythmias. The system includes a data processor configured to receive an electrical signal from a subject's heart for a plurality of heart beats, modeling QT interval (QTI) dynamics for the electrical signal for the predetermined period of heart beats, assessing a level of bounded-input bounded-output (BIBO) stability for the QTI dynamics, and predicting ventricular arrhythmias for the subject based on the QTI dynamics and BIBO stability for the predetermined period. The medical device can be, but is not limited to, a Holter monitor, a treadmill stress test device, an implantable cardioverter-defibrillators, or an ECG-based device, including devices that can monitor and/or respond in accordance with predictions of coronary arrhythmias according to an embodiment of the current invention.

Further embodiments of the current invention include a computer readable medium that includes stored executable instructions for execution by a computer. The executable instructions include instructions for receiving an electrical signal from a subject's heart for a plurality of heart beats, modeling QT interval (QTI) dynamics for the electrical signal for the predetermined period of heart beats, assessing a level of bounded-input bounded-output (BIBO) stability for the QTI dynamics, and, predicting ventricular arrhythmias for the subject based on the QTI dynamics and BIBO stability for the predetermined period.

Further embodiments of the current invention include computer programs configured to perform the methods of the current invention.

EXAMPLE

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

A method for assessing the level of BIBO stability in QTI dynamics, according to an embodiment of the present invention consists of two parts. First, the dependence of each QTI on several prior QTIs and RRIs is represented as an autoregressive model with exogenous input (ARX). Second, the BIBO stability of the ARX model is determined in the z-domain. The details of ECG data collection and annotation, ARX modeling of QTI dynamics, BIBO stability analysis in the z-domain, and data analysis are presented in the following sections.

A. ECG Recordings

ECG recordings from 15 patients were provided. All ECGs were recorded with specialized intensive care unit MARS telemetry system (GE Medical Systems, Milwaukee, Wis.); this system continuously records up to 28 hours of multi-lead ECG, sampled at 125 Hz. VT was identified in the ECG of each of these patients. The clinical demographics of the studied population, such as age, gender, diagnosis, beta-blocker usage, and antiarrhythmic drug therapy, are presented in Table 1.

TABLE I

CLINICAL DEMOGRAPHIC OF THE STUDIED POPULATION

| Age | 67.1 ± 12.7 |
|---|---|
| Gender (male) | 60% |
| Diagnosis | |
| Heart Failure | 20% |
| Arrhythmia | 60% |
| Acute Myocardial infarction (AMI) | 100% |
| Comorbidities | |
| Diabetes Mellitus | 26.7% |
| Hypertension | 53.3% |
| Beta blocker | 46.7% |
| Antiarrhythmic drug | 73.3% |

From each patient's multi-lead recordings, the recording with the best signal-to-noise-ratio was chosen for analysis to reduce the need of additional filtering. Cardiac events such as VT or VF were identified from these ECGs by the cardiologist. From the ECG recording of each patient, a ten-minute-long ECG trace was extracted immediately before the onset of a chosen VT, one per patient, and was used to construct the VT group. A control group was assembled in the same way, except that 10-minute ECG traces, again one per patient, were extracted 1 hour before the onset of the chosen VT, and at least 1 hour after any prior arrhythmia event. The choice of one hour before VT onset is supported by the findings of several clinical studies, which identified abnormal QTI dynamics and increased premature activation (PA) frequency as VT precursors minutes before the onset [23-25]. Within each group, each 10-minute recording was then divided into ten 1-minute ECG recordings (minECGs).

Figure 2:
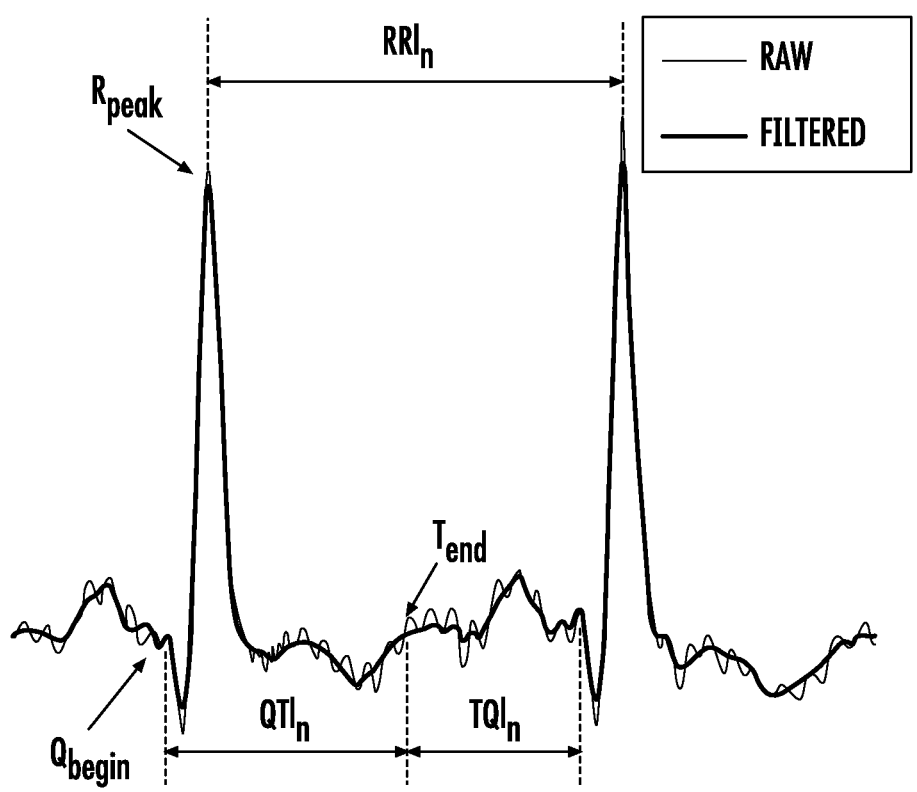
FIG. 2 illustrates a graphical view of an ECG recording before and after de-noising, and annotation of $Q_{begin}$, $R_{peak}$, $T_{end}$, QTI, and RRI.

In this example, noise filtering was not needed in most of the cases due to the good quality of the ECG recordings. However, in cases where noise was present in the signal, a wavelet-based de-noising filter was applied; the performance of this filter is illustrated in FIG. 2. Within each minECG, the beginning of the Q wave ($Q_{begin}$), the peak of the R wave ($R_{peak}$), and the end of T wave ($T_{end}$) were annotated to obtain QTI, TQI, and RR intervals (RRI), as illustrated in FIG. 2. $Q_{begin}$ and $R_{peak}$ were annotated following the detection of the QRS complex. $T_{end}$ was also annotated.

B. ARX Modeling of QTI Dynamics

An established approach, ARX, was used to model the QTI dynamics in each minECG:

$$QTI_n = \sum_{i=1}^{M} a_i \times QTI_{n-i} + \sum_{i=1}^{M} b_i \times RRI_{n-i} \quad (1)$$

where n is the beat number in the minECG; QTI and RRI are two discrete-time signals of the same length (the number of beats in the minECG); $QTI_n$, $QTI_{n-i}$, and $RRI_{n-i}$ are the values of the signal for beat n or n-i, respectively; $a_i$ and $b_i$ (i=1, . . . , M) are the weights (constants) with which each preceding QTI and RRI, respectively, contributes to $QTI_n$. M is the extent of the activation history (short-term memory) to be included in the ARX model. Notice that in this example, which differs from a QTI restitution study, RRI was used instead of TQI, because TQI is affected by the preceding QTI, and thus is not an independent exogenous input. Clearly, Equation 1 incorporates both restitution (dependence on the preceding RRI, $RRI_{n-1}$) and the contribution of activation history to QTI (dependence on the rest of the input variables).

The parameters of the ARX model were evaluated with Steiglitz-McBride iteration based on the entire QTI and RRI data sets for each minECG. The Steiglitz-McBride iteration identifies an unknown system based on both input and output sequences that describe the system's behavior. Using the RRI data set as an input, the output of each ARX model was computed and compared with the QTI data set to evaluate the accuracy of the model in predicting QTI dynamics. For each ARX model (i.e. each minECG), the value of M was determined by increasing it from 1, in steps of 1, and examining, at each step, whether an accurate prediction of the QTI dynamics of the minECG was achieved for that extent of the activation history. The value of M at which the prediction reached a pre-determined accuracy was denoted as $M_{max}$. The pre-determined accuracy in this example was that the mean square error between the predicted and the measured QTI was smaller than 5 ms$^2$. In addition to that, each ARX model was also validated with residual analysis.

C. Assessment of the Level of BIBO Stability in QTI Dynamics

The level of BIBO stability of each ARX model was assessed in the z-domain. To do so, the ARX model was first transformed from the time-domain into the z-domain, where z is a complex number. In the z-domain, the original function (Equation 1) becomes the transfer function H(z):

$$H(z) = \frac{QTI(z)}{RRI(z)} = g\frac{(z-\beta_1) \ldots (z-\beta_i) \ldots (z-\beta_M)}{(z-\alpha_1) \ldots (z-\alpha_i) \ldots (z-\alpha_M)} \quad (2)$$

where $\alpha_i$, $\beta_i$ (i=1, . . . , M), and g are coefficients (constants) derived from the weights $a_i$, and $b_i$ (i=1, . . . , M), while M is the number of components in H(z), which is the extent of the activation history M in the ARX model. When z is set equal to any of the $\alpha_i$ (i=1, . . . , M), one obtains a pole of the system; when z is set equal to any of the $\beta_i$ (i=1, . . . , M), one obtains a zero of the system; the system has M pole-and-zero pairs. A pole is canceled if it is equal to a zero. In this example, a pole is practically canceled by a zero if the difference between a pole and a zero is smaller than 0.05. According to the stability analysis theory, the system represented by the ARX (Equation 1) has BIBO-unstable dynamics if any pole falls outside of the unit circle |z|=1, i.e. the magnitude of the pole, |pole|, is >1.

D. Data Analysis

The stability of QTI dynamics in each minECG (i.e. of each ARX) was assessed as described above. A minECG was tagged as stable if stable QTI dynamics was identified for all M values, otherwise the minECG was tagged as unstable. High order (large M) ARX models with pole-zero cancellation were excluded from stability analysis in this example. A pole-zero cancellation suggests that a lower order (smaller M) model can be used to describe QTI dynamics. The increased M value in the high order ARX resulted in extra poles and zeros into Equation 2. These extra poles and zeros represent noise in the data but not the actual system. The noise can be caused by low sampling frequency (125 HZ) or other artifacts in the ECG recording, such as motion artifacts, poor lead-to-skin contact, or electromagnetic noise.

For each patient, the numbers of unstable minECGs in the VT and in the control groups were determined (denoted as $N_{us}$). It is well known that a PA could initiate unstable APD dynamics depending on the restitution slope, which is an expanding oscillation of APD around a fixed point in the APD restitution curve. Therefore the frequency of premature activation (PA) was also calculated for each 10-min ECG in each group and termed it as $f_{PA}$. Another index of QTI dynamics was also calculated, the QT variability index (QTVI). In the cases where the analyzed variables followed a normal distribution, paired t-test was used for comparisons between groups. Otherwise, Wilcoxon rank-sum test was used to compare the medians of the variables between groups. To ascertain whether $f_{PA}$ is related to QTI instability, the correlation coefficient between $f_{PA}$ and $N_{us}$ was calculated in both the VT group and the control group. The significance level of all these tests was 0.05.

Results

A. ARX Modeling of QTI Dynamics

The statistical summary of QTI, TQI, and RRI of both the VT and the control groups can be found in Table 2.

TABLE II

STATISTICAL SUMMARY OF RRI, QTI, AND TQI

|  | VT | Control | p |
|---|---|---|---|
| RRI (ms) | 659 ± 150 | 705 ± 157 | <0.01 |
| QTI (ms) | 401 ± 84 | 429 ± 65 | <0.01 |
| TQI (ms) | 258 ± 130 | 276 ± 141 | <0.01 |

Figure 3A:
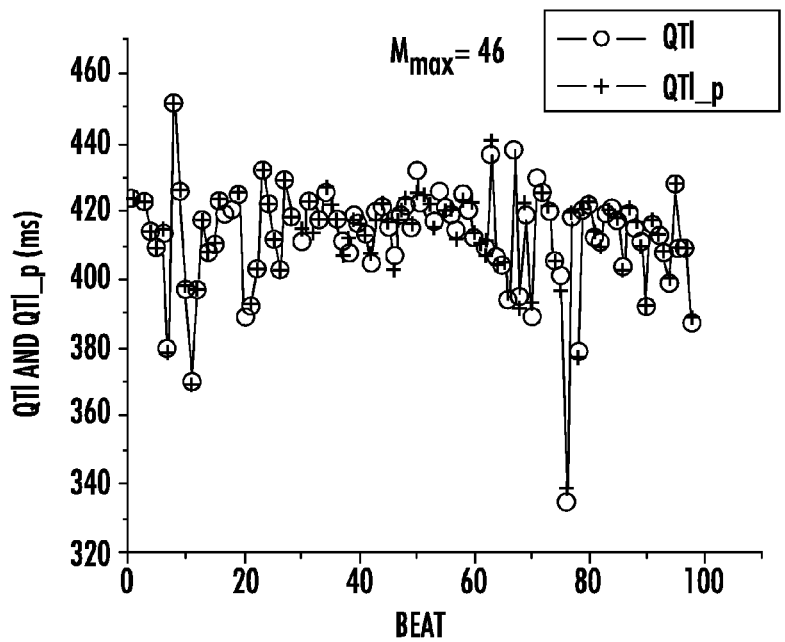
FIG. 3A illustrates a graphical view of predicted QTI (QTI_p) dynamics of a minECG, compared to QTI dynamics extracted from the same minECG for $M_{max}$=46.
Figure 3B:
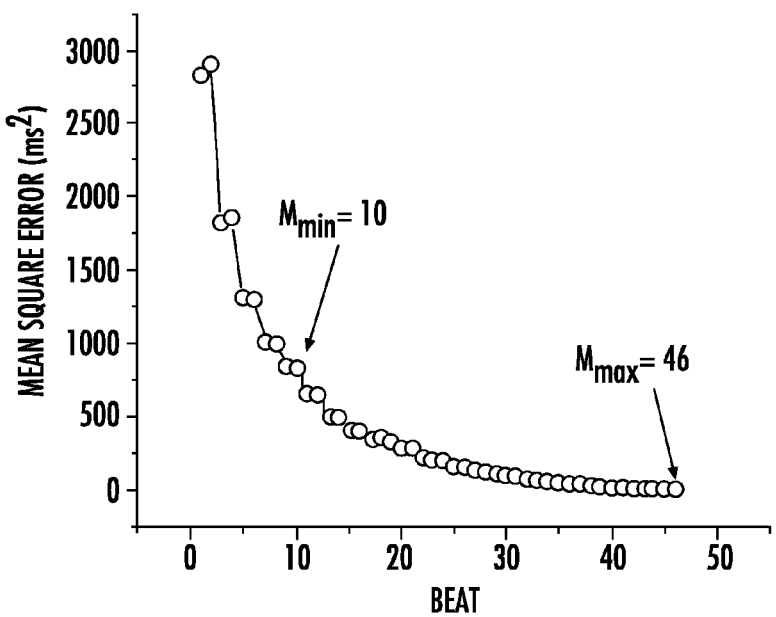
FIG. 3B illustrates dependence of prediction accuracy (mean square error) on the value of M. $M_{min}$ is the M at which unstable QTI dynamics was first identified.

For each minECG an ARX model was constructed. Using the RRI of each minECG as input, the output of the model was computed, as shown in FIGS. 3A and 3B. FIG. 3A demonstrates that an accurate prediction of QTI dynamics of an example minECG was achieved for $M_{max}$=46. The dependence of the prediction error on M is presented in FIG. 3B for the same minECG. The mean value of $M_{max}$ of the VT group was 37.8±8.8, which was significantly (p<0.01) different from that of the control group (32.1±8.16).

B. Instability Analysis

Example pole-zero plots resulting from the same minECG as in FIGS. 3A and 3B at M=10 and M=46 are illustrated in FIGS. 4A and 4B. The QTI dynamics of this minECG was unstable (FIGS. 4A and 4B), evidenced by several pairs of not-canceled-poles that are located outside of the unit circle. FIG. 4B shows that although M=10 does not result in a good QTI dynamics prediction (large mean square error in FIG. 3B), it nonetheless captures the instability in QTI dynamics accurately, as is evident by the presence of the two not-cancelled-poles (marked with arrows) outside of the unit circle. As M is increased to 46, the locations of the two poles in FIG. 4B remain the same as those in FIG. 4A (marked with arrows), with new not-cancelled-poles appearing at M=46. This result indicates that although accurate prediction of QTI dynamics requires a higher value of M ($M_{max}$), instability in QTI dynamics is first captured at a much smaller M, i.e. a shorter activation history is needed for accurate prediction of the instability in QTI dynamics than for the accurate prediction of QTI dynamics. The minimum M at which QTI instability is detected is termed $M_{mm}$. The mean $M^{min}$ for the VT group was 7.0±5.4, which was not significantly (p=0.75) different from that of the control group (7.4±5.5). Note that minECGs with stable QTI dynamics were excluded from the calculation of the mean $M_{min}$. This finding indicates that, for each patient, instability in QTI dynamics away from an arrhythmia event was determined by a similar number of preceding beats (i.e. extent of activation history) as before the onset of VT.

C. $N_{us}$, $f_{PA}$, and QTVI

In the VT group, the median of $N_{us}$ was significantly larger (p<0.02) than that in the control group, as illustrated in FIG. 5A. This indicates that more minECGs became unstable before VT onset as compared with those in control. The median of $f_{PA}$ of the VT group was significantly (p<0.03) higher than that of the control group, as illustrated in FIG. 5B. This indicates that more PAs took place before VT onset. The correlation coefficient between $N_{us}$ and $f_{PA}$ was found to be 0.85 (p<0.01) in the VT group and 0.69 (p<0.05) in the control group, indicating dependency between $N_{us}$ and $f_{PA}$ in the studied population. Finally, the difference in the median of QTVI was insignificant between the two groups (p=0.38).

Discussion

This example presents a novel methodology for assessing the level of BIBO stability in QTI dynamics from the clinical ECG recording. The results of this example show that the methodology is capable of capturing the BIBO-unstable QTI dynamics preceding VT onset. The results also revealed that VT onset and unstable QTI dynamics were correlated with the frequency of PAs. This finding is consistent with a previous study which reported that QTI dispersion was correlated with the frequency of ectopic beats in patients with acute myocardium infarction.

A. ARX vs. Restitution

In this example, an ARX model is used to describe the relationship between a given QTI and several prior QTIs and RRIs in the ECG; restitution relates the given QTI to its preceding TQI only. Without loss of generality, QTI restitution at a given TQI can be expressed as:

$$QTI_n = d \times TQ_{n-1} = d \times (RRI_{n-1} - QTI_{n-1}) \quad (3)$$

where d is the slope (a constant) of the QTI restitution curve at the given TQI. The transfer function of Equation 3 in the z-domain is:

$$H(z) = \frac{QTI(z)}{RRI(z)} = \frac{d}{z+d} \quad (4)$$

Figure 6:
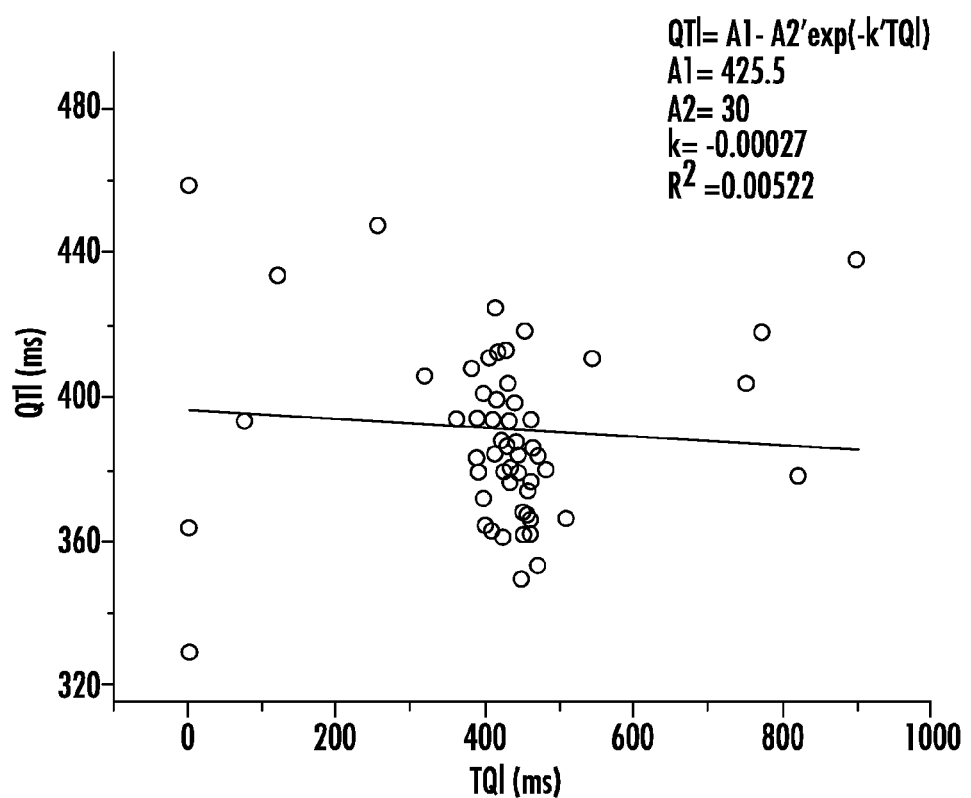
FIG. 6 illustrates a graphical view of an example of a QTI restitution relationship constructed from a minECG.

It is evident that Equation 3 is a reduced version of Equation 1 (i.e. the restitution is a reduced version of ARX) with $a_1 = -d$, $b_1 = d$, and all other parameters equal to 0. In this reduced case all activation history, except the preceding beat, is ignored. It is clear that when activation history cannot be ignored ($a_i \neq 0$, $b_i \neq 0$, i=1, . . . , M), restitution (Equations 3 and 4) is not an accurate means of describing QTI dynamics. This limitation can be further illustrated in FIG. 6, which presents the QTI restitution curve constructed from a minECG belonging to the VT group; the minECG was tagged as unstable using the present methodology. FIG. 6, illustrates that due to the large scatter in the data points, the goodness of the curve fit is unacceptable (R2<0.5). It has been reported in both animal and clinical studies that the outlier points in the restitution plot indicate increased arrhythmogenic risk, and thus should not be ignored. The present method includes these outlier points into the assessment of QTI instability, and thus constitutes a more comprehensive methodology, compared with restitution, to study the mechanisms of arrhythmia initiation.

Figure 7A:
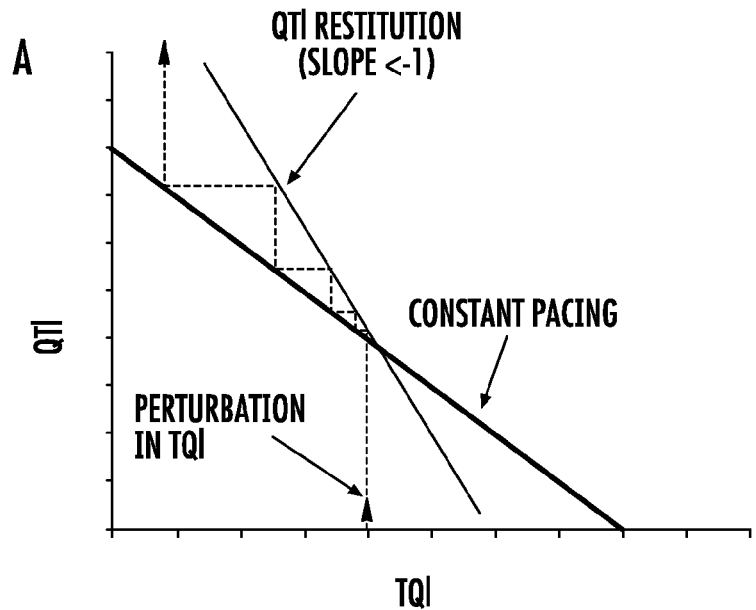
FIG. 7A illustrates a graphical view of a QTI restitution slope d<−1 with a small perturbation of TQI initiated diverging QTI dynamics.
Figure 7B:
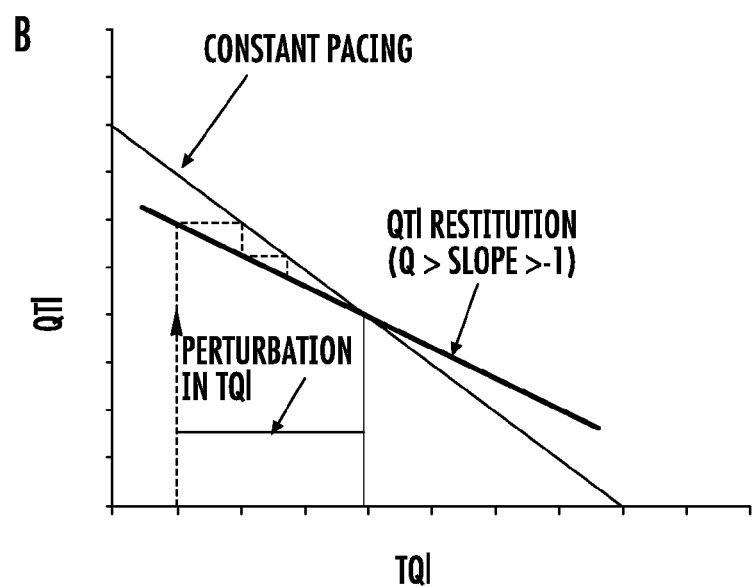
FIG. 7B illustrates a graphical view of a QTI restitution slope d>−1 with a large perturbation of TQI initiated converging QTI dynamics.

From Equation 4, it is evident that the reduced ARX model has only one pole, d. If the magnitude of d is larger than 1, which means either d>1 or d<−1, the ARX model is BIBO-unstable. In restitution analysis, a large restitution slope (>1) has been traditionally used as the instability criterion, while the effect of a negative restitution slope on APD or QTI dynamics has not been extensively studied, although there are ample experimental observations of it. In the present example, a general way to perform stability analysis of QTI dynamics is provided, which in the reduced case of Equation 4 also allows us to explore QTI dynamics under the conditions of negative restitution slope. The latter is presented graphically in FIGS. 7A and 7B. Following a perturbation in TQI (a bounded input), values of d<−1 resulted in unstable QTI dynamics in FIG. 7A, while in FIG. 7B a less negative value of d (0>d>−1) resulted in a stable QTI dynamics.

B. Comparison of the Present Methodology to QTVI

QTVI has been a valuable technique in arrhythmia risk stratification. QTVI characterizes, in a statistical manner, the relationship between QTI and RRI dynamics in the ECG recording, and provides an overall estimation of QTI variability, normalized by the magnitude of RRI variability. Elevated QTVI, which has been reported in diseased hearts, indicates QTI dynamics that is out of proportion to RRI dynamics. Although QTVI has been used as an index of repolarization lability, it is not a BIBO stability index, and thus is different from the present approach. Furthermore, ectopic beats are typically excluded from QTVI analysis, reflecting QTI dynamics under sinus rhythm only. However, ectopic beats could uncover arrhythmogenic unstable repolarization dynamics in the heart, much like the way a sudden short DI unmasks instability in APD when restitution is steep; the present methodology captures this instability. It is clear that QTVI and the present algorithm reveal different aspects of repolarization dynamics in the heart.

C. The Extent of Short-Term Memory

The results of this example provided new information regarding the extent of activation history that contributes to arrhythmogenesis. While ARX modeling has been used previously to assess the contributions of short-term memory and restitution to APD dynamics, the extent of the activation history was fixed at 4 beats; the studies concluded that APD dynamics cannot be fully explained with restitution and the chosen (4-beat) activation history. It has also been reported that the extent of activation history affecting QTI could be as long as 150 beats when only prior RRIs were considered. This number was reduced to 50 when a nonlinear component following a linear filter was used.

The present method uses M prior beats as activation history, where M is dynamically calculated, and could have a different value for each minECG. To accurately reproduce QTI dynamics, an $M_{max}$ number of prior QTIs and RRIs need to be incorporated in the ARX model (mean $M_{max}$<38), while the extent of activation history that contributes to QTI instability is much shorter (mean $M_{min}$<8). These new findings shed light on the contribution of short-term memory to arrhythmogenesis.

D. Clinical Significance

Both Nus and fPA increased before VT onset, which suggests a new avenue for clinical monitoring of arrhythmia onset by means of monitoring the values of these parameters. In addition, the present algorithm can be applied in the risk stratification of arrhythmia. Indeed, in this example a positive correlation between $N_{us}$ and $f_{PA}$ was observed. Because all the patients, the ECG recordings of whom were used in this example, had acute myocardial infarction and other cardiac diseases (Table 1), this positive correlation may not apply to the healthy heart. If this is proven to be the case, a positive correlation between frA and $N_{us}$ in the ECG would indicate arrhythmia risk, and could be used as a risk stratification index.

It is important to underscore that the present methodology for representing the ECG signal as an ARX uses different extents of activation history depending on the specific application of the methodology. If the goal of an application is to achieve an accurate (mean square error <5 m² in this example) prediction of QTI dynamics, then the largest number of beats, $M_{max}$, needs to be included in the ARX model. Alternatively, if the goal of an application is to determine whether QTI dynamics is BIBO-stable or not, then using $M_{min}$ number of beats in the ARX model is sufficient for this purpose, and this saves computational time. Again, $M_{min}$, represents the number of beats (out of the entire activation history, $M_{max}$) that are the major determinants of the BIBO stability in QTI dynamics.

E. Limitations

In this example, ectopic beats were not excluded from the analysis, and were treated in the same way as a sinus beat. It is necessary to keep PA in the study. The ARX modeling and stability analysis of QTI dynamics are based on the response of the model to perturbations in RRI, which is PA. Excluding PA will make it impossible to identify the ARX model correctly. However, the QRS width caused by an ectopic beat is typically different from that of a sinus beat. Sinus beats and ectopic beats also cause different T-wave morphologies. Therefore, the estimation of QTI stability in an ECG recording with a large number of ectopic beats might be less accurate than in a recording without ectopic beats.

An ARX model was used to describe the relationship between QTI and RRI dynamics. A limitation of this model is that ECG artifacts, such as motion artifacts, poor lead-to-skin contact, or electromagnetic noise, were included in the model. Another model, the autoregressive moving average model with exogenous inputs (ARMAX), is capable of decoupling the system dynamics from the artifacts. However, the parameter estimation of an ARMAX model usually requires a larger data set size, and could not be applied to a number of minECGs in this example.

Finally, short-term memory was represented here by a series of preceding QTIs and RRIs. This representation ignores the fact that the same QTIs may be associated with different T-wave shapes. Further studies need to be conducted to ascertain whether this limitation might have any impact on the results of this example.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of predicting ventricular arrhythmias, comprising:
   receiving an electrical signal from a subject's heart for a predetermined period of heart beats;

modeling QT interval (QTI) dynamics for the electrical signal for the predetermined period of heart beats using an autoregressive model with exogenous input (ARX model);

assessing a level of bounded-input bounded-output (BIBO) stability for the QTI dynamics;

predicting ventricular arrhythmias for the subject based on the QTI dynamics and BIBO stability for the predetermined period; and, activating a medical device to respond in accordance with the prediction of ventricular arrhythmia.

2. The method of claim 1 further comprising determining $Q_{begin}$, $R_{peak}$, and $T_{end}$ for the predetermined period of heart beats.

3. The method of claim 2 further comprising obtaining QTI, TQ interval (TQI), and RR interval for the predetermined period of heart beats.

4. The method of claim 1, wherein said receiving an electrical signal is at least one of receiving an electrocardiogram (ECG) or implantable cardioverter-defibrillator (ICD) electrogram signal.

5. The method of claim 3, wherein determining parameters of a QT interval dynamics model based on said QT intervals and RR intervals is determining parameters $a_i$ and $b_i$ in the following equation $$QTI_n = \sum_{i=1}^{M} a_i \times QTI_{n-i} + \sum_{i=1}^{M} b_i \times RRI_{n-i}$$

where M is a number of heart beats included in the determining and n is a heart beat number.

6. The method of claim 1 wherein assessing the MO stability further comprises transforming the QTI dynamics using the following equation, $$H(z) = \frac{QTI(z)}{RRI(z)} = g \frac{(z-\beta_1) \ldots (z-\beta_i) \ldots (z-\beta_M)}{(z-\alpha_1) \ldots (z-\alpha_i) \ldots (z-\alpha_M)}. \quad (2)$$

7. The method of claim 6 wherein there is BIBO instability if a magnitude of any pole of the equation is >1.

8. A medical device comprising a system for predicting ventricular arrhythmias, said system comprising a data processor configured to:

receive an electrical signal from a subjects heart for a predetermined period of heart beats;

model QT interval (QTI) dynamics for the electrical signal for the predetermined period of heart beats using an autoregressive model with exogenous input (ARX model);

assess a level of bounded-input bounded-output (BIBO) stability for the QTI dynamics;

predict ventricular arrhythmias for the subject based on the QTI dynamics and BIBO stability for the predetermined period; and, activate a medical device to respond in accordance with the prediction of ventricular arrhythmia.

9. The medical device of claim 8, wherein the data processor is further configured to determine $Q_{begin}$, $R_{peak}$, and $T_{end}$ for the predetermined period of heart beats.

10. The medical device of claim 9, wherein the data processor is further configured to obtain QTI, TQ interval (TQI), and RR interval for the predetermined period of heart beats.

11. The medical device of claim 8, wherein the electrical signal is at least one of receiving an electrocardiogram (ECG) or implantable cardioverter-defibrillator (ICD) electrogram signal.

12. The medical device of claim 8, wherein the data processor is further configured to determine parameters of a QT interval dynamics model based on said QT intervals and RR intervals is to determine parameters $a_i$ and $b_i$ in the following equation $$QTI_n = \sum_{i=1}^{M} a_i \times QTI_{n-i} + \sum_{i=1}^{M} b_i \times RRI_{n-i}$$

where M is a number of heart beats included in the determining and n is a heart beat number.

13. The medical device of claim 8, wherein the data processor is further configured to assess the BIBO stability further comprises transforming the QTI dynamics using the following equation, $$H(z) = \frac{QTI(z)}{RRI(z)} = g \frac{(z-\beta_1) \ldots (z-\beta_i) \ldots (z-\beta_M)}{(z-\alpha_1) \ldots (z-\alpha_i) \ldots (z-\alpha_M)}. \quad (2)$$

14. The medical device of claim 13, wherein the data processor is further configured to determine that there is BIBO instability if a magnitude of any pole of the equation is >1.

15. A fixed computer readable medium comprising stored executable instructions for execution by a computer, comprising executable instructions for:

receiving an electrical signal from a subjects heart for a predetermined period of heart beats;

modeling QT interval (QTI) dynamics for the electrical signal for the predetermined period of heart beats using an autoregressive model with exogenous input (ARX model);

assessing a level of bounded-input bounded-output (BIBO) stability for the QTI dynamics;

predicting ventricular arrhythmias for the subject based on the QTI dynamics and BIBO stability for the predetermined period; and, activating a medical device to respond in accordance with the prediction of ventricular arrhythmia.

16. The fixed computer readable medium of claim 15, further comprising determining $Q_{begin}$, $R_{peak}$, and $T_{end}$ for the predetermined period of heart beats.

17. The fixed computer readable medium of claim 16, further comprising obtaining QTI, TQ interval (TQI), and RR interval for the predetermined period of heart beats.

18. The fixed computer readable medium of claim 15, wherein said receiving an electrical signal is at least one of receiving an electrocardiogram (ECG) or implantable cardioverter-defibrillator (ICD) electrogram signal.

19. The fixed computer readable medium of claim 17, wherein determining parameters of a QT interval dynamics model based on said QT intervals and RR intervals is determining parameters ai and bi in the following equation $$QTI_n = \sum_{i=1}^{M} a_i \times QTI_{n-i} + \sum_{i=1}^{M} b_i \times RRI_{n-i}$$

where M is a number of heart beats included in the determining and n is a heart beat number.

20. The fixed computer readable medium of claim 15, wherein assessing the BIBO stability further comprises transforming the QTI dynamics using the following equation, $$H(z) = \frac{QTI(z)}{RRI(z)} = g\frac{(z-\beta_1) \ldots (z-\beta_i) \ldots (z-\beta_M)}{(z-\alpha_1) \ldots (z-\alpha_i) \ldots (z-\alpha_M)}. \quad (2)$$

21. The fixed computer readable medium of claim 15, wherein there is BIBO instability if a magnitude of any pole of the equation is >1.

* * * * *